United States Patent [19]

Goffredo

[11] 4,233,106
[45] Nov. 11, 1980

[54] METHOD FOR ION CONTROL OF SOLUTIONS

[75] Inventor: Daniel L. Goffredo, Riverton, N.J.

[73] Assignee: Chemcut Corporation, State College, Pa.

[21] Appl. No.: 55,990

[22] Filed: Jul. 9, 1979

Related U.S. Application Data

[62] Division of Ser. No. 865,859, Dec. 30, 1977.

[51] Int. Cl.² .............................................. C23F 1/02
[52] U.S. Cl. .................................. 156/627; 134/10; 156/640; 156/642; 156/666
[58] Field of Search ............... 156/626, 627, 642, 640, 156/345, 656, 659, 666; 134/10, 104, 108

[56] References Cited

U.S. PATENT DOCUMENTS

| | | | |
|---|---|---|---|
| 3,844,857 | 10/1974 | Chiang | 156/627 |
| 3,964,956 | 6/1976 | Snyder | 156/627 X |
| 4,058,431 | 11/1977 | Haas | 156/627 |

*Primary Examiner*—William A. Powell
*Attorney, Agent, or Firm*—Paul & Paul

[57] ABSTRACT

A system is provided for control of ion concentration (as for example in pH or redox control), for use for example in etching articles, wherein other features such as specific gravity control are also provided. The ion concentration control is provided with cleaning and recalibration features. In a specific embodiment, provision is made for adding ammonia to an etching solution and for continuously monitoring the pH of the system. Visual indicators are provided for operator observation of fluid flow through various lines, generally by windows being provided in the cabinet apparatus. A particular electrode cell is disclosed as a prominent feature of ion concentration control.

2 Claims, 5 Drawing Figures

METHOD FOR ION CONTROL OF SOLUTIONS

This is a division of application Ser. No. 865,859, filed Dec. 30, 1977.

BACKGROUND OF THE INVENTION

In the art related to chemical treatment, wherein fluids are utilized for various purposes, including but not limited to etching and redox (oxidation-reduction) treatments, and generally in systems where ion concentration needs to be controlled, various techniques have been developed. Some of these techniques have addressed themselves to pH control of etching solutions and the like, as well as to specific gravity control. Some types of etching equipment to which such controls are adaptable are for example those disclosed in U.S. Pat. No. 4,015,706 to Daniel L. Goffredo and Conrad Dale Shakley.

In various types of chemical treatment, particularly in the etching or chemical machining of articles, for example, printed circuit boards, the articles are delivered along a conveyor through an etching chamber in which they are sprayed with an etchant. In instances in which the articles being treated contain copper, and the etching solution is being used to remove some of the copper from the articles, the etching solution may for example be ammonium hydroxide and ammonium chloride with a chelating or complexing agent, (generally with cupric ions at the beginning of the reaction to initiate oxidation). As etching continues, there is a build-up of copper ions in the solution that tend to use the etchant and etchant may be lost to atmosphere by evaporation. Consequently, it becomes necessary to periodically (or continuously) add a replenisher solution to the etchant. A typical replenisher solution would be additional ammonium chloride and ammonium hydroxide with a chelating or complexing agent. During the etching operation, the vaporizing of ammonia tends to reduce the pH of the etching solution. Consequently, it becomes necessary to make a correction, that will raise the pH of the solution to the desired level. This can be done by the addition of ammonia to the etchant. In unsophisticated operations, when the pH dropped to an undesired level, the etchant would merely be discarded and a new batch utilized. However, economic factors dictate that this is an undesirable procedure. Consequently, the practice developed whereby the lost ammonia was replaced by adding aqua ammonia (ammonium hydroxide) to the etchant which diluted the etchant, thereby generally interfering with specific gravity control. Some attempts were made to improve upon the situation by adding anhydrous ammonia.

The desirability of pH control was noted, so that anhydrous ammonia could be added automatically. However, it was observed that with the loss of ammonia and the lowering of pH, copper precipitates in the form of complex salts would tend to clog nozzles, gears, and pumps, such that there would cease to be any effective operation of the pH controller. Such precipitates furthermore, interfered with the operation of the etching operation in general.

Where the pH controllers involved the use of electrodes, the precipitation of salts described above would tend to foul the electrodes. This situation would especially occur during overnight or weekend shutdowns of the etching apparatus when the ammonia gas escaped from the etchant in larger quantities, causing the pH to drop, which brought on the precipitation. Upon startup, the electrodes would be fouled and the control system could not function properly. Proper operation of such a system was entirely dependent upon operator attention to properly cleaning electrodes.

SUMMARY OF THE INVENTION

The present invention is directed to the control of ion concentration by the use of sensor cells that have provision for periodic (or continuous), automatic assessment of the ion concentration level of a treating solution, together with provision for either manual or automatic periodic (or continuous), automatic cleaning and convenient recalibration of the sensor cells. In specific form, the sensor cells include electrodes and are operative to control the pH of an etchant, preferably in a system also involving specific gravity control of the etchant. The present invention is also directed to the control of redox, and control of other treatment solutions. Other features of the invention involve the provision of visual indication of various fluid (liquid or gas) flows, such as of replenisher solution, ion-corrective fluid, and the treatment fluid itself in the sensor cell, generally by the use of transparent materials and windows in cabinets of the apparatus.

It is, accordingly, a primary object of this invention to provide a novel ion concentration control for treatment solutions and the like.

It is another object of this invention to provide novel apparatus incorporating such ion concentration control.

It is a further object of this invention to provide a novel system and apparatus for the continuous etching and treatment of articles wherein the pH of the etching solution is automatically and continuously controlled, also with provision for manual or automatic self-cleaning and calibrating, both with and without specific gravity control.

It is a further object of this invention to provide apparatus for automatically and continuously controlling oxidation-reduction potential also with provision for manual or automatic self-cleaning and calibrating of sensor cells, both with and without specific gravity control.

It is another object of this invention to provide a system and apparatus wherein continuous etching may be accomplished, where the control of ammonia loss and aeration may be effected.

It is a further object of this invention to provide novel sensor cells that allow for their cleaning for removal of precipitates therefrom, and with provision for recalibration of the sensors.

It is another object of this invention to provide for visual observation of fluid flow in connection with the sensors described in the objects set forth above, through the use of substantially transparent windows in the apparatus for operator observation, as well as for the use of observation windows generally in the apparatus for visual observation of fluid flow of various types.

It is another object of this invention to provide sensor cells that lend themselves to operator observation of precipitate build-up in the cells.

Other objects and advantages of the present invention will be readily apparent to those skilled in the art of reading the following brief descriptions of the drawings figures, detailed description of the preferred embodiments, and the appended claims.

BRIEF DESCRIPTION OF THE DRAWING FIGURES

DETAILED DESCRIPTION OF PREFERRED EMBODIMENT

Figure 1:
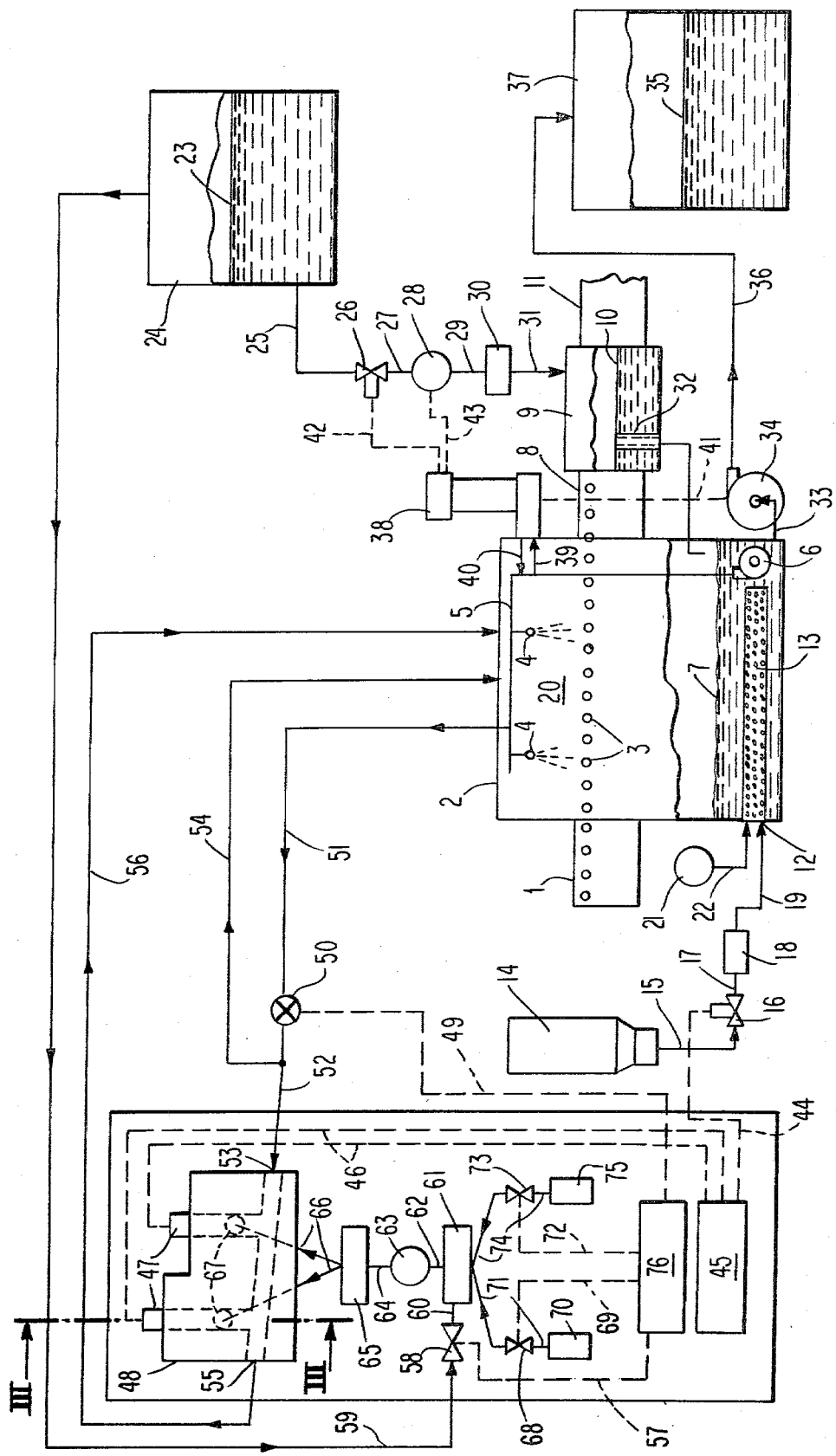
FIG. 1 is a schematic illustration of one embodiment of the system of this invention, illustrating the various components of the apparatus and their interconnections.

Reference is now made to FIG. 1 which illustrates a preferred embodiment and system of operation embodying the principles contemplated by the inventor for carrying out his invention. It will be understood that, while reference hereinafter may be made to etching equipment, systems and the like, that similar principles as embraced in the apparatus and system of the present invention are employed in other types of chemical treatment, wherein control of ion concentration is desirable. For example, but without being limited thereto, oxidation-reduction systems, such as for redox systems may likewise employ controls of the type disclosed herein. Furthermore, systems of the type disclosed herein may also be used for the monitoring of rinse water within an etching system, or, for any other application where rinse water is employed, or even for any other type of liquid treatment.

The articles to be etched will, in accordance with this invention, often be printed circuit boards, printed circuit film or the like, but it will be understood that the present invention may be addressed to any other type of articles, whether or not employing copper in their construction.

Articles to be etched are carried along the rollers of a conveyor 1, from left to right as viewed in FIG. 1, through an etch module 2 where they are sprayed with an etching or other treatment solution that is delivered above the conveyors 3 through spray nozzles 4 that in turn are supplied from an etchant header 5 to which etchant is provided by means of a pump 6 disposed at the lower end of the module 2, and fed by etchant 7 in a sump at the lower end of the module 2, all of which comprise a means for delivering etchant to the articles. These articles are then transported from the etching chamber 2 on a conveyor 8, and then to a flood rinse module 9, where they are rinsed in a replenisher 10, and are then carried from the flood rinse module 9 to be transported therefrom on conveyor 11. In a preferred embodiment, the articles contain copper to be etched therefrom, and both the etchant and the replenisher are alkaline and contain ammonium chloride and ammonium hydroxide and chelating or complexing agents. Oxygen necessary to this continuous system will be supplied to the etch module as air. At initial start-up, the alkaline etchant also contains cupric ions for oxidation of the copper.

In an alkaline solution, the ammonium hydroxide and the ammonium chloride and the cupric ions and oxygen in the air, will oxidize copper to form complex copper ammonium salts. The dissolving of the copper from the articles by oxidation consumes ammonium ions present and raises the specific gravity of the etchant. By removing the complex copper ammonium salts from the etchant and by adding fresh ammonium hydroxide and ammonium chloride to the etchant, in the presence of oxygen, the etching process becomes continuous. In this etching system, ammonia tends to leave the etchant, and this ammonia loss causes the pH of the etchant to drop. When the pH of the etchant drops below a certain value, such as 8.0, copper ammonium salts tend to precipitate on the etched articles and on the nozzles and openings in the etching apparatus. Anhydrous ammonia is therefore admitted to the etch module to raise the pH of the etchant. Anhydrous ammonia is preferred in this invention because it does not contain water which will unnecessarily dilute the etchant.

The etch module 2 has an etch module intake opening 12, on the side of the module, near the bottom, through which anhydrous ammonia enters the etch module. A hollow perforated pipe, called a sparger 13 is attached to the intake opening, to disperse the ammonia into the etchant, as a means for compensating for the drop in pH of the etchant.

The ammonia is drawn from an ammonia tank 14 along a conduit 15 through an ammonia supply solenoid valve 16, then along a conduit 17 through a transparent ammonia flow indicator 18, where the flow of ammonia can be visually observed, and then along a conduit 19 through the etch module intake opening 12 through the sparger 13 and into the etchant 7.

In this system, cupric ions oxidize the copper to cuprous ions and are themselves reduced to cuprous ions. Oxygen is then used in this reaction to oxidize the cuprous ions to cupric ions, which will then oxidize more copper.

Oxygen is introduced into the etchant 7, either as a part of the atmosphere 20 in the upper part of the etch module chamber or through an air pump 21 (optional) which is attached along conduit 22 to the etch module intake opening 12.

Alkaline replenisher 23 which contains ammonium chloride and ammonium hydroxide is stored in a replenisher supply tank 24, from where it passes along conduit 25 through a replenisher supply solenoid valve 26, then along conduit 27 through a replenisher pump 28, where it is pumped along conduit 29 through a transparent replenisher flow indicator 30 where the flow of the replenisher can be visually observed and then along conduit 31 into the flood rinse module 9. Some replenisher 10 remains in the flood rinse module where it is used to rinse etched articles that have been carried through it from the etch module. If the etched articles were rinsed in water or an acid, etchant remaining on the articles would likely be precipitated on these articles. Some of the replenisher from the flood rinse module is purposely allowed to flow into the etch module through an overflow pipe 32, whose upper opening is in the flood rinse module, and whose lower opening is in the etch module.

As a part of the etching process, some of the etchant, with acquired copper ions, is drawn out of the etch module 2 through an etch module exhaust outlet 33 which is attached to a scavenge pump 34 which pumps the used etchant 35 along conduit 36 to a spent etchant tank 37.

The flow of alkaline replenisher from the replenisher supply tank 24 to the flood rinse module 9 is controlled by an automatic Baume specific gravity sensorregulator 38 which is connected to the etchant header 5 of the etch module 2 along supply and return conduits 39 and 40 respectively for sampling and assessing the specific gravity of the etchant 7. The etchant feed to conduit 33 for the pump 34 may be controlled by conventional techniques, such as by use of a float valve (not shown) that actuates the pump 34 upon the etchant level in the tank 2 reaching a predetermined level. As an option, the specific gravity control means 38 may activate the scavenge pump 34 as shown in FIG. 1, via control line 41 to pump used etchant 35 to the spent etchant tank 37 along conduit 36.

Specific gravity control means 38 is connected to and regulates the replenisher supply solenoid valve 26 via control line 42 to open the valve 26 when the specific gravity of the etchant in the etch module 2 falls below a predetermined value. Specific gravity control means 38 is also connected along control line 43 to the replenisher pump 28, which it also activiates at the same time, when the replenisher supply solenoid valve 26 is thus opened, and the replenisher 23 flows into the sump tank at the bottom of the flood rinse module 9 until it overflows through the overflow pipe 32 into the etch module 2.

Thus, in this invention, the specific gravity of the etchant is controlled automatically by a specific gravity regulator 38 which samples and assesses for specific gravity, a portion of the etchant, and when the specific gravity of the etchant indicates that the amount of complex copper salts in the etchant is too great, the specific gravity regulator will open a replenisher valve allowing fresh replenisher containing ammonium hydroxide and ammonium chloride to enter the etching system and may optionally open an exhaust outlet in the etch module removing those complex salts. When the replenisher with ammonium hydroxide and ammonium chloride enters the etching system it first goes into the flood rinse tank and then when that rinse tank is full, the replenisher overflows into the etch module. The rinse solution contains ammonium hydroxide and ammonium chloride, which is alkaline. It will be noted that replenisher is required for the etch module as fresh etchant, to replace the etchant being used in the etching process.

The opening and closing of the ammonia supply solenoid valve 16 is controlled along control line 44 by the pH regulator 45 which is connected along control lines 46 to a pair (or more) of pH electrodes 47 in the sensor cell 48 for obtaining pH indicator signals from those electrodes. Either manually, or if desired upon automatic cue from the timing sequence controller 76 along control line 49, etchant sample solenoid valve 50 is opened and a sample of etchant is drawn along conduit 51 connected with header supply line 5, from the etchant 7 in the etch module 2 and is passed through the etchant sample solenoid valve 50 along conduit 52 into a sample intake opening 53 in the sensor cell 48 where it comes into contact with the electrodes 47. Any excess etchant sample is returned to the etch module through a bleed line 54. After contacting the electrodes, the etchant sample leaves the sensor cell through a sensor cell outlet 55 to be returned to the etch module along conduit 56. As an unpreferred alternative the etchant sample can be discarded when it leaves the sensor cell, rather than returned to the etch module.

These electrodes 47 transmit a pH signal along control lines 46, indicating that pH to the pH regulator 45 which is pre-set to open or close the ammonia supply solenoid valve 16 upon receipt of various pH indicator signals. When the pH of the etchant falls below 8.0, some of the etchant salts tend to precipitate, thus interfering with the etching process. When the ammonia supply solenoid valve is opened, and anhydrous ammonia enters the etch module, the pH of the etchant rises to a better etching pH level, between 8.0 and 10.0, or preferably between 8.5 and 9.0, with an optimum being 8.5. The pH regulator can be pre-set so that it will automatically open the ammonia supply solenoid valve 16 when it receives a signal from the electrodes in the sensor cell that the pH of the etchant sample is below 8.0 (or another pre-set value) and it will close that solenoid valve when it receives a signal that the pH of the etchant sample is over 10.0 (or other pre-set value).

It will thus be seen that the valve 16 will be opened or closed in automatic fashion, depending upon the value of pH as detected through the sensor 48, and as dictated by the regulator 45, between the pre-set limits (generally 8.0 and 10.0). Thus the sampling and assessing of the pH of the etchants in the sensor cell and the subsequent transmission of pH etchant information from the sensor cell to the pH regulator is continuous, in generally adding ion-corrective solution to the etchant delivering means (to the tank at the bottom of etch chamber 2).

In a automatic embodiment of this invention the pH electrodes in the pH sensor cell are automatically cleaned and recalibrated by the introduction to the electrodes in the pH sensor cell, first of a replenisher solution containing ammonium chloride and ammonium hydroxide, then followed by distilled water, both functioning as cleaning liquids, then followed by a buffer or calibration (standardizing) liquid of known pH which will permit this pH sensorregulator system to be recalibrated for the next assessment of a new etchant sample.

In both the manual and automatic modes, the cleaning of the electrodes and of the cell itself and the convenient recalibration of the electrodes 47 in the sensor cell 48 is accomplished by serially contacting those electrodes first with the alkaline replenisher which removes the remaining etchant samples from the electrodes, then with distilled water which removes the replenisher from the electrodes, then with the buffer solution.

In the automatic mode of cleaning and recalibration, in order to clean and recalibrate the electrodes 47 in the sensor cell 48, the controller 76 can be pre-set first to close the etchant sample solenoid valve 50 via control line 49, then to open and close via control line 57 the replenisher sensor solenoid valve 58 connected to replenisher tank 24 by conduit 59 for a pre-set time to allow replenisher 23 to enter, along conduit 60, the first sensor manifold 61 from where it is piped along conduit 62 to the sensor pump 63, which is a self-priming bellows pump, where the replenisher is pumped along conduit 64 into a second sensor manifold 65 and from there along conduits 66 into both cleaning-recalibrating solutions openings 67 in the sensor cell 48 where the replenisher contacts the electrodes 47 and then leaves the sensor cell through the sensor cell outlet 55 to the etch module 2 along conduit 56. When the replenisher sensor solenoid valve 58 has been automatically closed by the controller 76 (via control line 57) the regulator 76 then automatically opens and closes, for a pre-set time, the distilled water solenoid valve 68 (via control line 69) causing distilled water to be transmitted from a distilled water tank 70 along conduit 71 to the first sensor manifold 61, then along conduit 62 to the sensor pump 63, then along conduit 64 to the second sensor manifold 65, then along conduits 66 through both cleaning-recalibration solutions openings 67 in the sensor cell 48 so that the distilled water contacts the electrodes 47 in the sensor cell. The distilled water then leaves the sensor cell through sensor cell outlet 55 and is transmitted to the etch module 2 along conduit 56. When the controller 76 has automatically closed the distilled water solenoid valve 68 via control line 69, the controller 76 then automatically opens and closes for a pre-set time, along control line 72 the buffer solenoid valve 73 allowing a buffer solution to be transmitted along conduit 74 from the calibration liquid supply (known pH buffer) tank 75 through the buffer solenoid valve 73 to the first sensor manifold 61, then along conduit 62 to the sensor pump 63, then along conduit 64 to the second sensor manifold 65 and then along conduits 66 through both cleaning recalibration solutions openings 67 in the sensor cell 48 where the buffer solution contacts the electrodes 47 in the sensor cell 48. The buffer solution then leaves the sensor cell through the sensor cell outlet 55 and is transmitted to the etch module 2 along conduit 56. When the buffer solution of the known pH has contacted the electrodes 47, the controller 76 can be recalibrated to compensate for electronic drift or for any other factors, to assess pH values accurately. The distilled water tank 70 and the known pH buffer tank 75 will preferably be substantially transparent so that the amount or level of their contents can be visually observed. A liquid guage can be attached to each of these tanks, if desired, to automatically emit a signal to an operator when supply levels become too low.

Thus it will be seen that the serial delivery of the replenisher and the distilled water and the known pH buffer solution to the sensor cell is automatically controlled by the controller 76 which automatically controls three separate solenoid valves, one connected to the replenisher tank, one connected to a distilled water tank, and the third connected to a buffer tank. Moreover, it will thus be apparent that each of the two cleaning and one recalibrating solutions is serially passed through a first sensor cell manifold before being pumped to a second manifold connected to the sensor cell. The use of the first manifold allows the system and apparatus to use one pump to serially pump three different solutions separately to the second sensor manifold. The controller 76 may be a timing device set to operate the solenoid valves in the desired sequence. In manual operation, the same sequence is also followed. It will moreover be apparent that the second sensor manifold 65 functions as a flow splitter, whereby flow delivered from the pump 63 through conduit 64 is split into two different conduits 66 for delivery to two separate electrodes.

In etchant reclamation, the used etchant 35 contains complex copper ammonium salts. The sensor cell can be then used to control the reduction of those copper ions in the used etchant 35, and the copper ions can be reduced to copper. By using either oxidation-reduction (redox) or pH electrodes in the sensor cell, the sensor cell 48 can also be used to monitor rinse water contamination, as well as the ionic values of other solutions. It will therefore be clear that the present regulatorsensor techniques applying not only to various types of etchants, but any treatment solutions in which ion concentration control is desired. Other etchant solutions that can be controlled with redox include copperchloride reoxidized with chlorine gas, copperchloride reoxidized with hydrogen peroxide, copper sulfate and sulfuric acid reoxidized with hydrogen peroxide, and ferric chloride (used to etch steel) reoxidized with chlorine gas.

Figure 2:
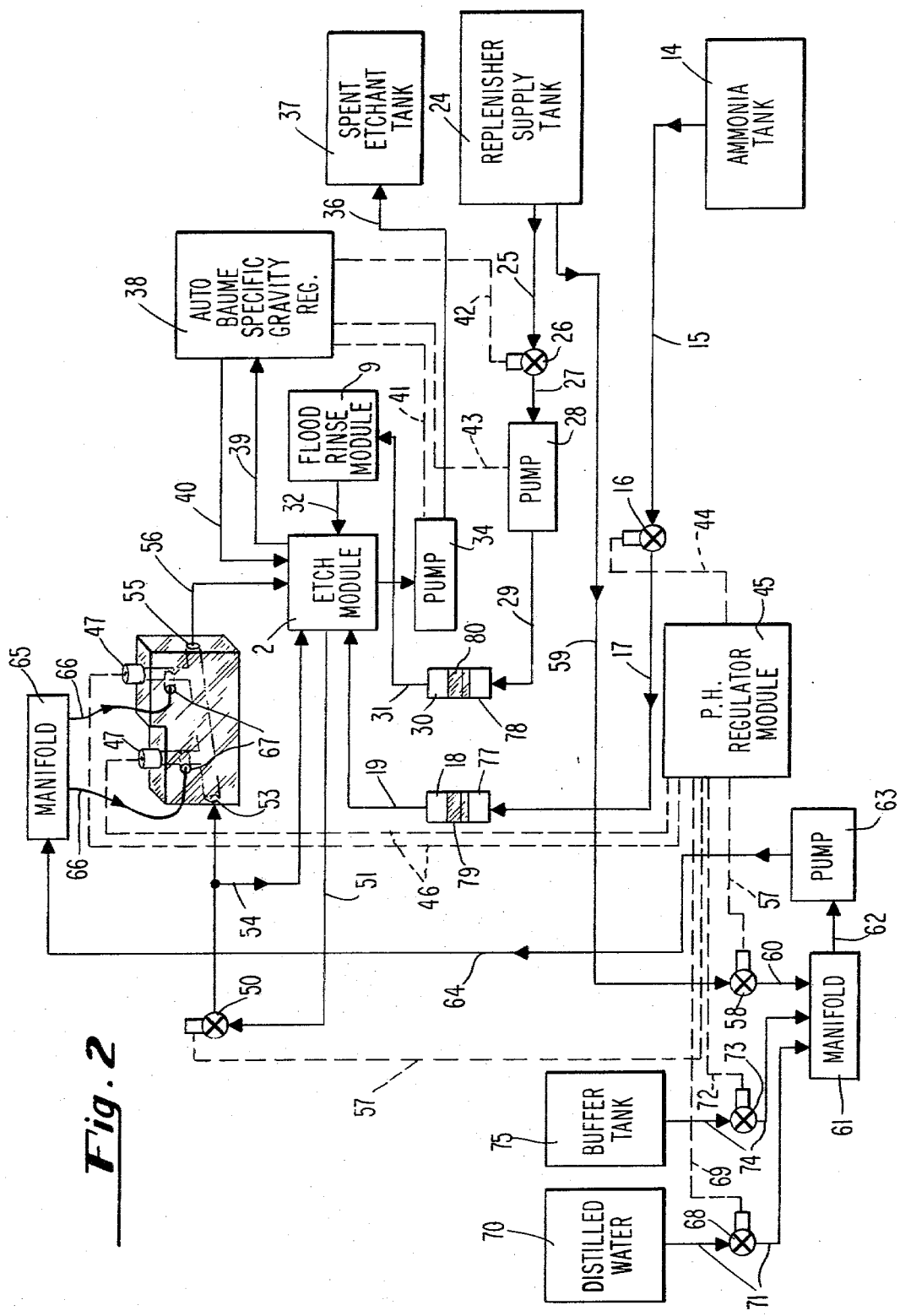
FIG. 2 is a block diagram view of the system illustrated in FIG. 1, also illustrating a sensor cell in accordance with this invention, in perspective illustration.

With particular reference to FIG. 2, it will be noted that a convenient diagram illustrates the flow arrangement of fluids in the preferred embodiment of this invention, with the control lines for the various valves, pumps, etc. being illustrated as dotted lines and with the solid lines illustrating flow in the direction of the arrows.

Figure 5:
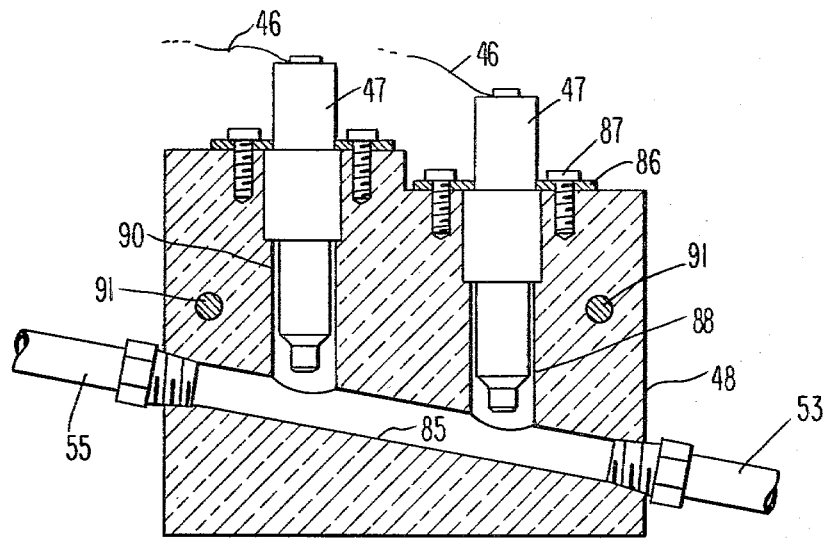
FIG. 5 is a longitudinal vertical sectional view taken through the sensor cell in accordance with the present invention, with the view being taken generally along the line V—V of FIG. 3.
Figure 3:
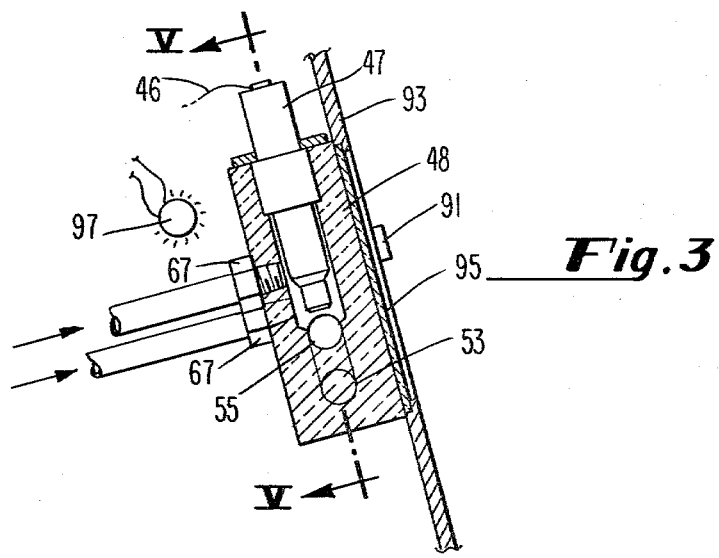
FIG. 3 is a vertical sectional view taken through a front panel of the control module and sensor cell in accordance with this invention, also illustrating a visual observation port for the sensor cell, with the view being taken generally along the line III—III of FIG. 1.

With particular reference now to FIGS. 3 and 5, the sensor cell 48 is illustrated as comprising a transparent molded one-piece (or two-piece split formed, if desired), structure of preferably transparent or a substantially transparent material of construction, to allow an operator to observe buildup of precipitates therein, and to observe flow therethrough of etchant delivered from conduit 51 along longitudinal cell conduit 85. It will be noted that the electrodes 47 are secured at the upper end of the cell 48 by conventional threaded fasteners 87 or any other suitable means. It will be noted that the lower ends of the electrodes 47, that communicate with etchant, replenisher, water or buffer solution are disposed in transverse conduits 88 and 90 that communicate at their lower ends with conduit 85, inside the cell 48.

The cell 48 will generally be carried against a front wall or cabinet panel 93 of a control module, being mounted thereto by suitable fasteners 91 passing through the cell 48. A window cutout 94 is provided in the panel 93, for visual observation of the cell 48, and with a transparent window plate 95 being provided in the cabinet's panel 93, against which the cell 48 is mounted.

In order to facilitate visual obervation through the window 94, an electric light 97 may be provided behind the cell, for illumination of flow therethrough, and for illumination of precipitate buildup. If desired, the sensor cell can also be provided with one or more temperature sensing electrodes (not shown) connected to the regulator 45, to notify the pH regulator of the temperature of the etchant samples, and with the regulator 45 then being provided with suitable circuitry or the like for making corrections on the basis of temperature in some pre-determined manner.

Figure 4:
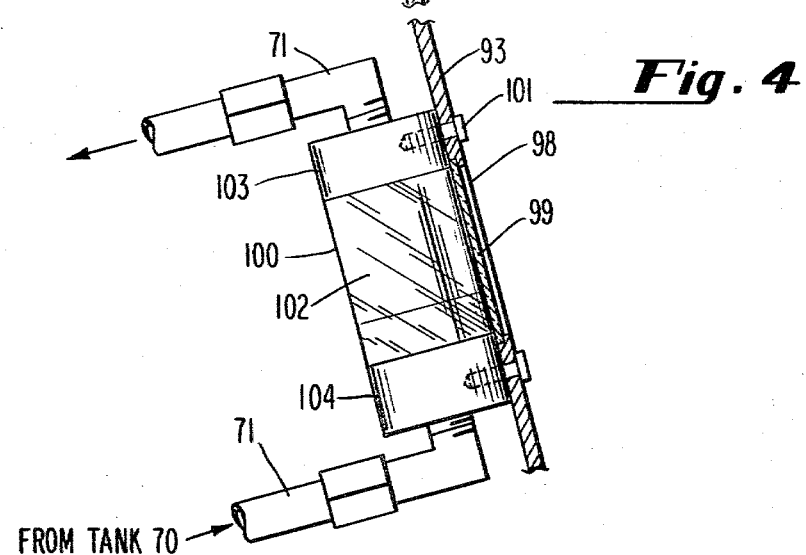
FIG. 4 is a vertical sectional view taken through a portion of the front panel of the control module of this invention, and also through a visual observation port for a transparent section of a conduit line from a distilled water tank or the like, and with the conduit line being illustrated in elevation.

With reference now to FIG. 4, if desired, the panel 93 of the control cabinet may be provided with another window 98 having a transparent cover 99 therein. In that portion of line 71 between the valve 68 and the manifold 61, there would be provided a transparent section 100 of the line 71, as illustrated in FIG. 4. This could be mounted directly behind the observation window 98, such transparent section being fastened and secured to the panel 93 by suitable threaded fasteners 101 or the like. The transparent portion 100 may be constructed as a cylinder, generally having a transparent glass, plastic, or the like sleeve 102, having end caps 103, 104, which are connected to inlet and outlet portions of the line 71 as illustrated in FIG. 4, for supplying inlet and outlet water from tank 70 to the chamber or transparent section 100. It will, therefore, be seen that, when desired water in line 71 may be visually observed through the window 98.

A similar observation window (not shown) may be provided for observation of buffer fluid solution through conduit 74, between the valve 73 and manifold 61.

Also, while it will be noted that in the illustration of FIG. 4 the flow of water from the tank 70 (similarly the flow of buffer fluid solution from tank 75) appears to be upward, it will be understood that such may be the case if the flow of fluids from the tanks 70 and 75 are delivered by pumps (not shown) if desired. As an alternative, the fluids delivered from tanks 70, 75 may be delivered under pressure for facilitating upward flow. As a further alternative, the tanks 70, 75, can be maintained at a generally higher vertical level than the pump 63 for gravity feed if desired.

It will further be noted that observation windows in panels similar to that of FIG. 4 are preferably provided as conduit viewports for flow indicators 18 and 30. The flow indicators 18 and 30 are each generally constructed from transparent tubing sections 77 and 78, respectively, having flow responsive plugs 79 and 80, respectively, of smaller diameter than the inside of the tubing sections 77 and 78; and disposed therein to be lifted from plug seats (not shown) when there is flow through the indicators 18 and 30, for visual observation by an operator when there is flow of ammonia gas or replenisher, respectively.

The regulator means 45 may be constructed of suitable electronic or other circuitry or the like, by conventional techniques, to accomplish the valve opening, valve closing, ion concentration measuring, and calibration against a known solution, all of which are known individually in the art. The regulator 45 may be pre-programmed to call for these various functions serially and, if desired, may be set for automatic operation in conjunction with the timing sequence of controller 76, when the timing sequence of valves 50, 58, 68 and 73 is being automatically controlled. As such, the system lends itself to convenient, automatic operation.

It will be understood that various modifications may be made in the details of construction, the placement of hardware and other various components of the present invention, their mountings on cabinets, panels for achieving desired visual observation, or within the spirit and scope of the invention. Moreover, it will be apparent that various modifications may be made in the use and function of the system of the present invention for the purpose of accommodating various types of treatments, all within the spirit and scope of the invention as defined in the appended claims.

What is claimed is:

1. In a method of treating articles with an etchant or other treatment solution, wherein a chamber is provided for treating articles therein, wherein treatment solution is delivered to articles in said chamber, wherein the ion concentration of the treatment solution is detected in a sensor cell and communicated to a regulator for controlling the amount of an ion-corrective fluid that is added to the treatment solution to compensate for deviation from desired ion concentration so detected, the improvement comprising, shutting off the supply of treatment solution to the sensor cell, providing replenisher treatment solution to the sensor cell for cleaning the cell, then rinsing the cell with water, then passing a standardizing solution of known ion concentration through the cell and recalibrating the regulator against the solution of known ion concentration.

2. The method of claim 1, including the step of sampling the treatment solution to determine its specific gravity and adding an amount of replenisher treatment solution to the treatment solution to compensate for deviation from desired specific gravity so detected.

* * * * *